(12) United States Patent
Levin (10) Patent No.: US 7,756,576 B2
(45) Date of Patent: Jul. 13, 2010

(54) POSITION SENSING AND DETECTION OF SKIN IMPEDANCE

(75) Inventor: Michael Levin, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 205 days.

(21) Appl. No.: 11/213,040

(22) Filed: Aug. 26, 2005

(65) Prior Publication Data

US 2007/0060832 A1 Mar. 15, 2007

(51) Int. Cl.
  *A61B 5/04* (2006.01)
  *A61B 8/00* (2006.01)
  *A61B 5/05* (2006.01)
(52) U.S. Cl. .................. 600/547; 600/372; 600/373; 600/386; 600/424
(58) Field of Classification Search .......... 600/547, 600/372–373, 386, 424
  See application file for complete search history.

(56) References Cited

U.S. PATENT DOCUMENTS

| | | | |
|---|---|---|---|
| 5,436,513 A * | 7/1995 | Kaye et al. ............... | 307/71 |
| 5,443,489 A | 8/1995 | Ben-Haim | |
| 5,697,377 A | 12/1997 | Wittkampf | |
| 5,899,860 A | 5/1999 | Pfeiffer et al. | |
| 5,944,022 A * | 8/1999 | Nardella et al. ............. | 128/899 |
| 5,983,126 A | 11/1999 | Wittkampf | |
| 6,047,208 A * | 4/2000 | Flower ........................ | 604/20 |
| 6,050,267 A * | 4/2000 | Nardella et al. ............. | 128/899 |
| 6,095,150 A | 8/2000 | Panescu et al. | |
| 6,301,496 B1 * | 10/2001 | Reisfeld ..................... | 600/407 |
| 6,308,093 B1 * | 10/2001 | Armoundas et al. ........ | 600/509 |
| 6,456,864 B1 | 9/2002 | Swanson et al. | |
| 6,496,715 B1 | 12/2002 | Lee et al. | |

FOREIGN PATENT DOCUMENTS

WO  WO 96/05768 A1  2/1996

* cited by examiner

*Primary Examiner*—Max Hindenburg
*Assistant Examiner*—Sean P Dougherty
(74) *Attorney, Agent, or Firm*—Louis J. Capezzuto (57) ABSTRACT

Apparatus and methods are provided for determining in near realtime the position of a probe placed within a living body. Electric currents are driven between one or more electrodes on the probe and electrodes placed on the body surface. The impedance between the probe and each of the body surface electrodes is measured, and three-dimensional position coordinates of the probe are determined based on the impedance measurements. Dynamic compensation is provided for changing impedance of the body surface and its interface with the electrodes, resulting from such causes as electrode peel-off and changes in moisture and temperature. The compensation improves the accuracy of, inter alia, medical procedures, such as mapping the heart or performing ablation to treat cardiac arrhythmias.

6 Claims, 6 Drawing Sheets

POSITION SENSING AND DETECTION OF SKIN IMPEDANCE

BACKGROUND OF THE INVENTION

1. Field of the Invention

This invention relates to sensing the position of an object placed within a living body. More particularly, this invention relates to detection and compensation for artifacts experienced during position sensing of a probe in a living body using impedance measurements.

2. Description of the Related Art

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

Many such position sensing systems have been developed or envisioned in the prior art. Some systems involve attaching sensors to the internal object in the form of transducers or antennas, which can sense magnetic, electric, or ultrasonic fields generated outside of the body. For example, U.S. Pat. Nos. 5,697,377 and 5,983,126 to Wittkampf, whose disclosures are incorporated herein by reference, describe a system in which three substantially orthogonal alternating signals are applied through the subject. A catheter is equipped with at least one measuring electrode, and a voltage is sensed between the catheter tip and a reference electrode. The voltage signal has components corresponding to the three orthogonal applied current signals, from which calculations are made for determination of the three-dimensional location of the catheter tip within the body.

Similar methods for sensing voltage differentials between electrodes are disclosed by U.S. Pat. No. 5,899,860 to Pfeiffer; U.S. Pat. No. 6,095,150 to Panescu; U.S. Pat. No. 6,456,864 to Swanson; and U.S. Pat. Nos. 6,050,267 and 5,944,022 to Nardella, all of whose disclosures are incorporated herein by reference.

SUMMARY OF THE INVENTION

Embodiments of the present invention provide efficient apparatus and methods for determining in near realtime the position of a probe placed within a living body. In these embodiments, electric currents are driven between one or more electrodes on the probe and electrodes placed on the body surface. In this manner, the impedance between the probe and each of the body surface electrodes is measured, and three-dimensional position coordinates of the probe are determined based on the impedance measurements. Dynamic compensation for changing local impedance of the body surface and its interface with the electrodes is performed using a novel electrode design and driving circuit. Such impedance variations can be sudden, from causes such as electrode peel-off, or can be more gradual, due to changes in skin moisture or skin temperature. The compensation improves the accuracy of, inter alia, medical procedures, such as mapping the heart or performing ablation to treat cardiac arrhythmias.

The invention provides a method for position sensing in a living body, which is carried out by positioning a first electrode and a second electrode on at least one of a plurality of surface locations, wherein the second electrode is electrically isolated from the first electrode, determining a local first impedance by passing a first electrical current from the first electrode to the second electrode via the surface of the body at the one surface location, inserting a probe including at least one probe electrode into the body, passing a plurality of second electrical currents between the probe electrode and at least one of said first electrode and said second electrode via the surface of the body at respective ones of the surface locations, and determining second impedances to the second electrical currents. The method is further carried out responsively to the second impedances by determining internal body impedances of the second electrical currents by compensating for the first impedance, and determining position coordinates of the probe responsively to the internal body impedances.

In an aspect of the method, positioning comprises adhering an electroconductive surface pad containing the first electrode and the second electrode to the one surface location.

In another aspect of the method, compensating is performed by determining a component of one of the second impedances that is caused by the pad and the surface at the one surface location and subtracting the component from the one second impedance.

According to a further aspect of the method, the first electrical current and the second electrical currents are alternating currents.

According to yet another aspect of the method, determining the first impedance includes arranging the first electrode in a series circuit with the second electrode, and determining the second impedances includes arranging the first electrode in a parallel circuit with the second electrode.

Still another aspect of the method includes repeating determining a local first impedance at predetermined intervals.

According to an additional aspect of the method, inserting the probe includes performing a medical treatment on the body using the probe.

According to one aspect of the method, the probe includes a catheter, and performing the medical treatment comprises mapping the heart of the body.

The invention provides an apparatus for position sensing, including a probe having at least one probe electrode, which is adapted to be inserted into a body of a living subject. A plurality of electroconductive body surface patches are fixed to a body surface at respective surface locations. The body surface patches each comprise a first electrode and a second electrode, and the second electrode is electrically isolated from the first electrode. The apparatus includes electrical circuitry for arranging the first electrode in a series circuit with the second electrode in a calibration mode of operation and for arranging the first electrode in a parallel circuit with the second electrode in a sensing mode of operation, and a controller, which is operative to control the electrical circuitry, and which is adapted to be coupled to the probe and to the body surface patches so as to pass first electrical signals through the first electrode and the second electrode thereof in the calibration mode of operation, and to pass respective second electrical signals through the body between the probe electrode and the body surface patches. The controller is operative in the calibration mode of operation to determine a local electrical impedance of the body surface and of an interface thereof with a respective one of the body surface patches, and to determine position coordinates of the probe in the sensing mode of operation by measuring respective impedance characteristics of the second electrical signals. The impedance characteristics of the second electrical signals are adjusted by the controller according to respective instances of the local electrical impedance.

According to another aspect of the apparatus, the controller is adapted to maintain a constant voltage between each of the surface locations and the probe electrode, and to measure respective impedance characteristics by measuring currents at the constant voltage.

According to a further aspect of the apparatus, the controller is adapted to maintain a constant current between each of the surface locations and the probe electrode, and to measure respective impedance characteristics by measuring voltages at the constant current.

According to yet another aspect of the apparatus, the probe is adapted to perform a medical treatment on the subject.

According to still another aspect of the apparatus, the body surface patches comprise an adhesive layer that contacts the body surface.

In an additional aspect of the apparatus, the controller is operative to alternate the calibration mode of operation and the sensing mode of operation responsively to time intervals measured by an interval timer.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

System Overview

Figure 1:
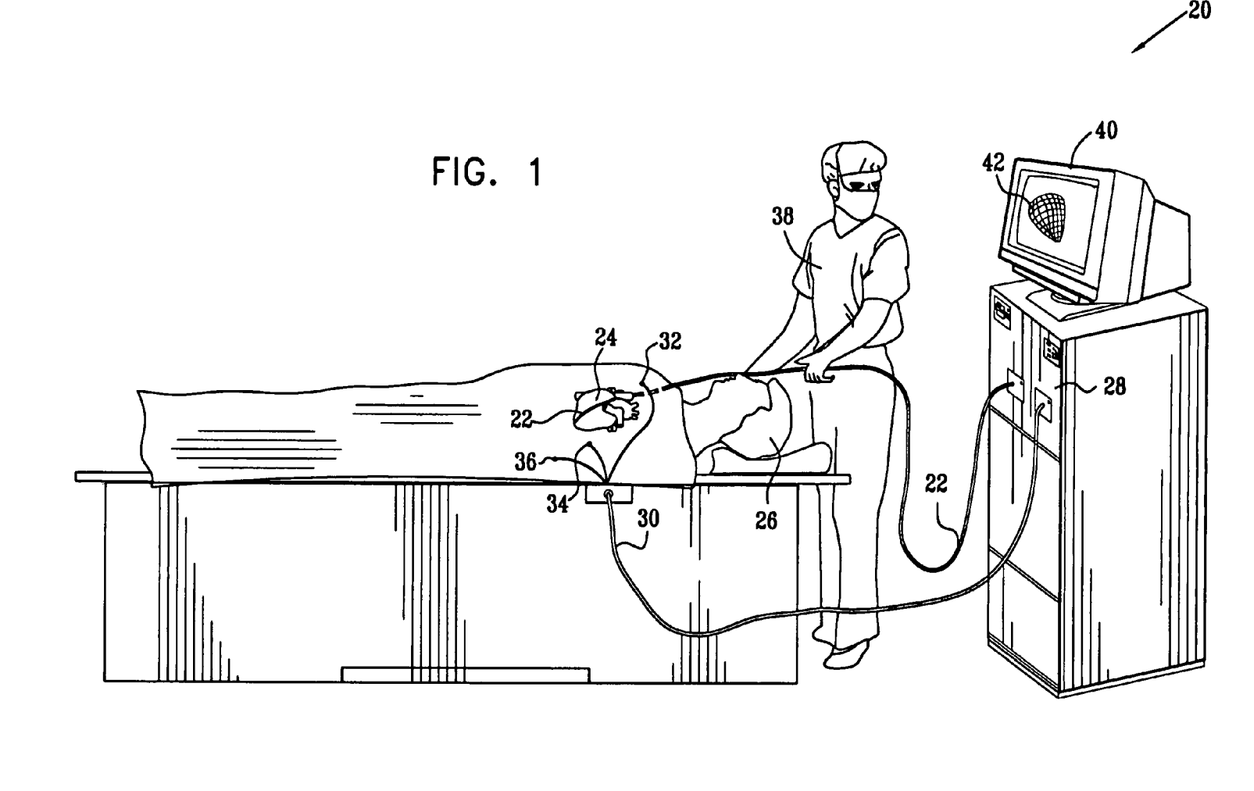
FIG. 1 is an illustration of a position sensing system, which is constructed and operative in accordance with a disclosed embodiment of the invention.

Turning now to the drawings, reference is initially made to FIG. 1, which is an illustration of a position sensing system 20, which is constructed and operative in accordance with a disclosed embodiment of the invention. The system 20 is used by a user 38 in determining the position of a probe, such as a catheter 22, which is inserted into an internal body cavity, such as a chamber of a heart 24 of a subject 26. Typically, the catheter is used for diagnostic or therapeutic medical procedures, such as mapping electrical potentials in the heart or performing ablation of heart tissue. The catheter or other intrabody device may alternatively be used for other purposes, by itself or in conjunction with other treatment devices.

The distal tip of the catheter 22 comprises one or more electrodes, described below. These electrodes are connected by wires through the insertion tube of the catheter 22 to driver circuitry in a control unit 28, as described below. The control unit is connected by wires through a cable 30 to body surface electrodes, which typically incorporated in adhesive electroconductive body surface patches 32, 34, 36. The patches 32, 34, 36 may be placed at any convenient locations on the body surface in the vicinity of the probe. For example, for cardiac applications, the patches 32, 34, 36 are typically placed around the chest of the subject 26.

Typically, the patches 32, 34, 36 are placed on external surfaces of the body, but in some applications some or all of them could be placed on internal surfaces. There is no special requirement regarding the orientation of patches relative to each other or to the coordinates of the body, although greater accuracy may be achieved if the patches are spaced apart, rather than clustered in one location. There is no requirement that the placement of the patches be along fixed axes. Consequently, patch placement can be determined so as to interfere as little as possible with the medical procedure being performed. The control unit 28 determines position coordinates of the catheter 22 inside the heart 24 based on an adjusted impedance measured between the catheter 22 and the patches 32, 34, 36. Details of the adjustment are given below. The control unit drives a display 40, which shows the catheter position inside the body. The catheter 22 may be used in generating a map 42 of the heart, for example, an electrical map, wherein the electrodes on the catheter are used alternately for position sensing and for measuring electrical potentials generated in the heart tissue. The catheter position may be superimposed on this map or on another image of the heart.

Figure 2:
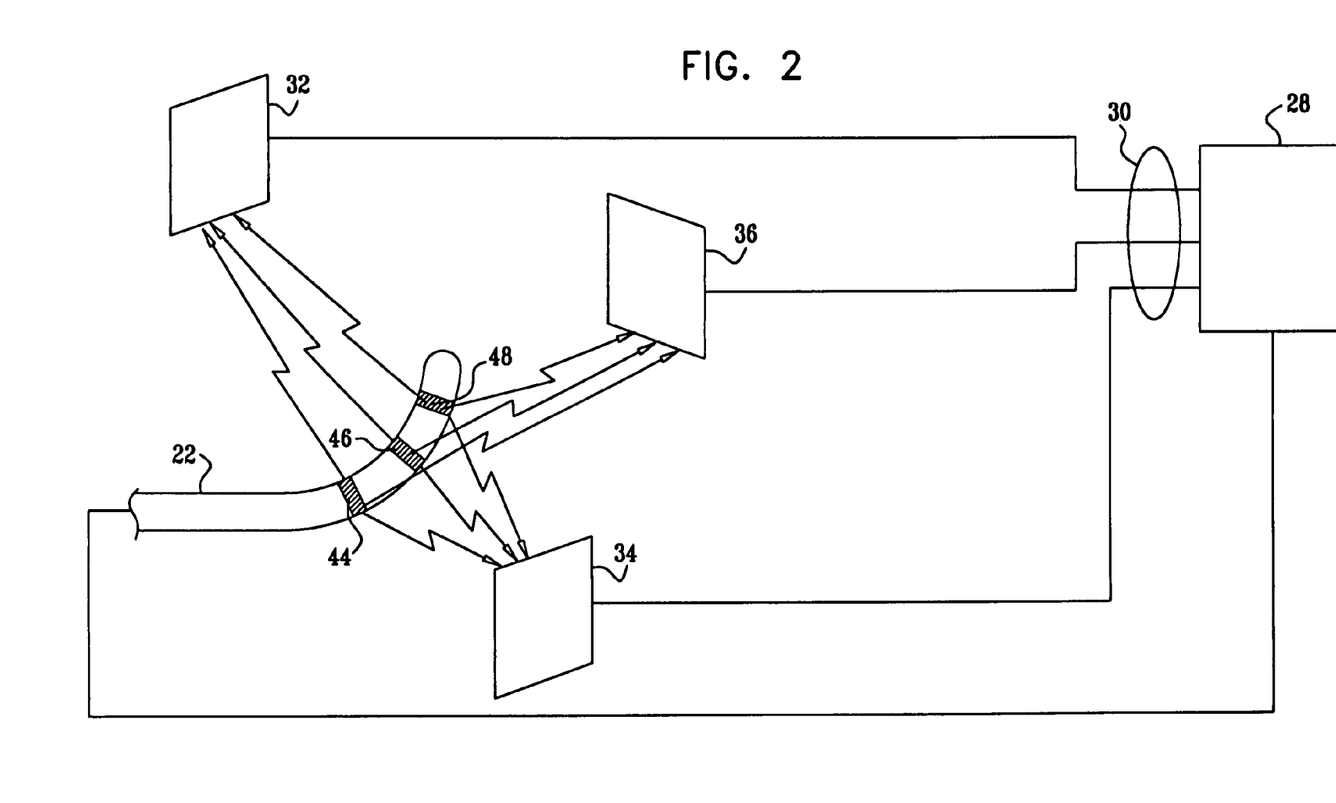
FIG. 2 is a schematic view of a catheter used in the system shown in FIG. 1, which is constructed and operative in accordance with a disclosed embodiment of the invention.

Reference is now made to FIG. 2, which is a detailed schematic view of the catheter 22 (FIG. 1), which is constructed and operative in accordance with a disclosed embodiment of the invention. Interaction is shown in FIG. 2 between electrodes 44, 46, 48 disposed on the catheter 22 and the patches 32, 34, 36. The electrodes 44, 46, 48 may be of any suitable shape and size, and may be used for other purposes, as well, such as for electrophysiological sensing or ablation. In the pictured embodiment, each of the electrodes 44, 46, 48 communicates with all of the patches 32, 34, 36 (FIG. 1). The control unit 28 (FIG. 1) drives a current between each catheter electrode and all body surface electrodes, and uses the current to measure the impedances between the catheter electrode and the patches 32, 34, 36. Based on the measured impedances, the control unit 28 determines the catheter position relative to the body surface electrodes. Alternatively, greater or smaller numbers of electrodes may be used. For example, the control unit 28 may be set to multiplex the currents between one catheter electrode and multiple body surface electrodes. As another example, more than three body surface electrodes may be used for enhanced accuracy.

Figure 3:
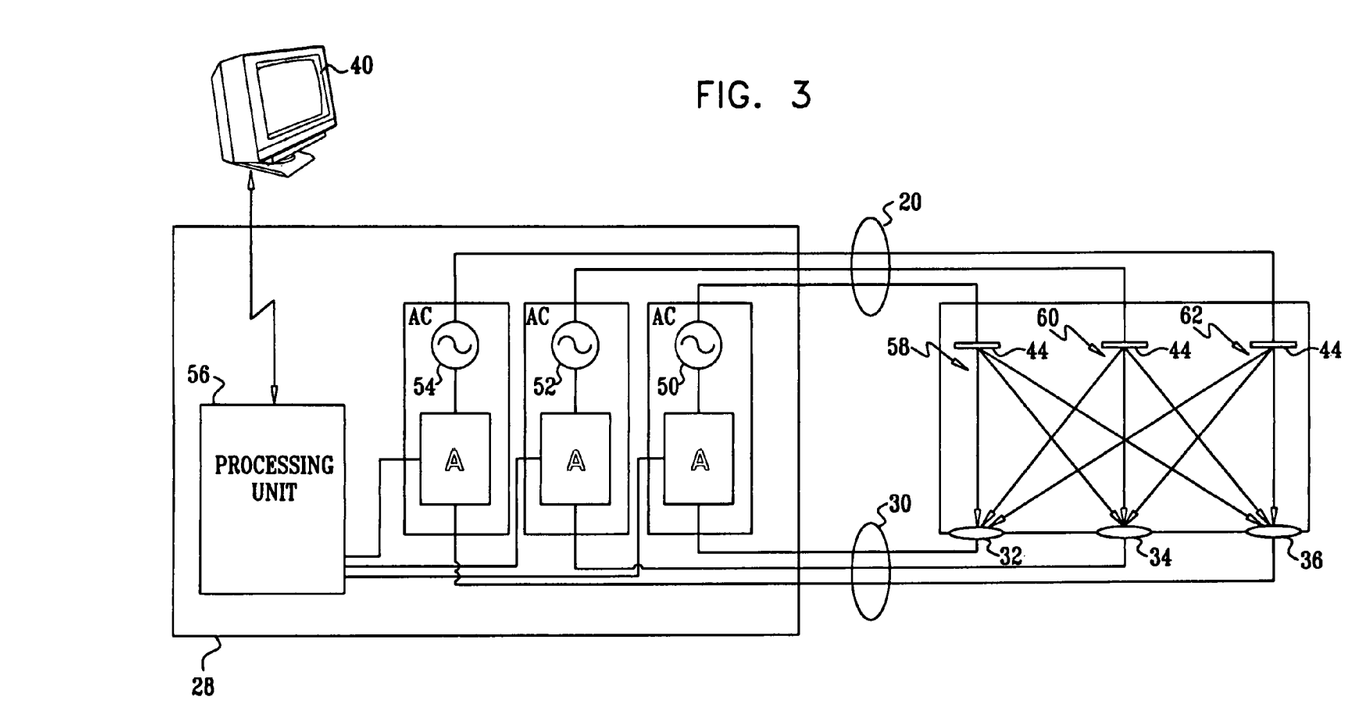
FIG. 3 is a block diagram showing electrical circuitry and control of the system shown in FIG. 1, in accordance with a disclosed embodiment of the invention.

Reference is now made to FIG. 3, which is a block diagram showing elements of the system 20 (FIG. 1) in accordance with a disclosed embodiment of the invention. The control unit 28, described above, comprises circuitry for driving currents and for measuring impedance. Each of three circuits 50, 52, 54 drives a current through a closed loop consisting of a catheter electrode and the body surface of the patches 32, 34, 36. Specifically, the circuit 50 drives a current through body tissue 58, which lies between the electrode 44 and the patches 32, 34, 36; the circuit 52 drives a current through body tissue 60, which lies between the electrode 46 and the patches 32, 34, 36; and the circuit 54 drives a current through body tissue 62, which lies between the electrode 48 and the patches 32, 34, 36. Each of the currents generated by the driver circuits may be distinguished by setting the circuits 50, 52, 54 to operate at different frequencies.

Each of circuits 50, 52, 54 measures the electrical impedance in its respective loops through the body tissues 58, 60, 62. These impedance readings are passed to a controller or processing unit 56, which uses the readings to calculate the position coordinates of the catheter relative to the body surface electrodes. Based on these position coordinates, the processing unit 56 then generates the real-time information appearing on the display 40, as described above.

In one embodiment of the invention, the circuits 50, 52, 54 generate constant voltage signals. The circuits 50, 52, 54 measure the currents flowing through the respective loops to determine impedances, which are then used to calculate the position coordinates.

In a second embodiment of the invention, the circuits 50, 52, 54 generate constant current signals. Measurement of the voltage across the current drivers can therefore be measured by the processing unit 56 to determine impedances, which are used to calculate position coordinates.

In either of the two embodiments described above, the impedance measured is proportional to the distance between the electrode and the patch. These distances may then be used to triangulate the position at the tip of the catheter 22 using well known methods, described, e.g., in U.S. Pat. No. 5,443,489, and PCT Patent Publication WO 96/05768 to Ben-Haim et al., whose disclosures are incorporated herein by reference. The measurement accuracy may be further improved by making initial reference measurements with the catheter at known anatomical locations (i.e., landmarks within the heart), or by using a separate, reference catheter at a known location to calibrate the impedance scale.

The system 20 (FIG. 1) represents an embodiment of the invention as it may be used in a catheter-based procedure for diagnosis or treatment of conditions of the heart, such as arrhythmias. The system 20 can be used, as well, in the diagnosis or treatment of intravascular ailments, which may involve angioplasty or atherectomy. The principles of system 20 may also be applied, mutatis mutandis, in position-sensing systems for the diagnosis or treatment of other body structures, such as the brain, spine, skeletal joints, urinary bladder, gastrointestinal tract, prostrate, and uterus.

Body Surface Patches

Figure 4:
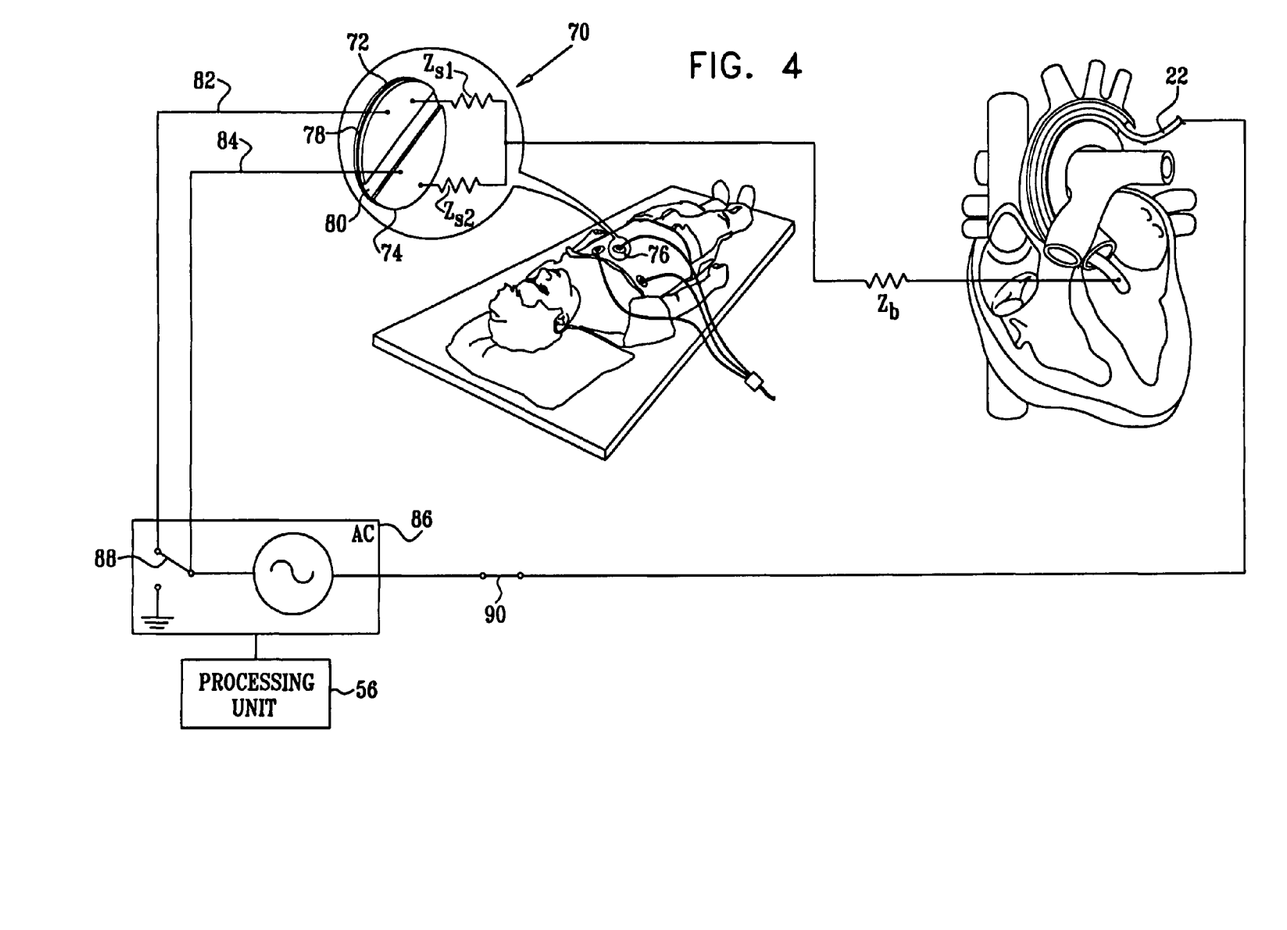
FIG. 4 is a schematic diagram showing an electroconductive body surface patch and associated electrical circuitry configured in a sensing mode of operation in accordance with a disclosed embodiment of the invention.

Reference is now made to FIG. 4, which is a schematic diagram showing an electroconductive body surface patch 70 and its associated electrical circuitry configured for a sensing mode of operation. The body surface patch 70 is used as one or more of the patches 32, 34, 36 (FIG. 1). Typically, all of the patches 32, 34, 36 are realized as instances of the body surface patch 70. In order to perform the impedance measurements described above accurately, a stable baseline of body surface impedance, e.g., skin impedance, is required. Using the body surface patch 70 in accordance with the present invention reduces the impact that body surface impedance variations have on the position measurements of the catheter 22 (FIG. 1).

The body surface patch 70 is an adhesive electrode pad, comprising two electrically isolated body surface electrodes 72, 74, which are adhered to a body surface 76 by an adhesive layer 78. The electrodes 72, 74 are separated by an insulator 80. As was described above, the catheter 22 (FIG. 2) passes a current through the subject's body to the electrodes 72, 74. Dual wires 82, 84 convey current from the respective electrodes 72, 74 to the processing unit 56 and to a driver 86. The driver 86 can be the AC voltage or current source in a respective one of the circuits 50, 52, 54 (FIG. 3). Alternatively, the driver 86 can be a different source. When the position of the catheter 22 is being sensed, the wires 82, 84 are electrically connected by a switch 88, so that the electrodes 72, 74 are arranged in parallel with the driver 86, as shown in FIG. 4. REM POLYHESIVE™ II Patient Return Electrodes, available from Valleylab, 5920 Longbow Drive, Boulder, Colo. 80301-3299, are suitable for use as the body surface patch 70.

The total impedance Z seen by the driver 86 is the sum of the local electrical impedance $Z_{local}$ of the body surface and its interface with the body surface patch 70, and the intrabody impedance $Z_b$ between the catheter 22 and the body surface 76. The components of the local electrical impedance $Z_{local}$ are the impedance $Z_{s1}$ of the electrode 72 and the body surface 76, and impedance $Z_{s2}$ of the electrode 74 and the body surface 76 in parallel:

$$Z_{local} = \frac{Z_{s1} Z_{s2}}{Z_{s1} + Z_{s2}}.$$

The total impedance Z computed by the processing unit 56 can thus be approximated by the equation $$Z = Z_b + \frac{Z_{s1} Z_{s2}}{Z_{s1} + Z_{s2}}.$$

In this mode of operation, the body surface patch 70 functions as a conventional, single-piece body surface electrode.

Figure 5:
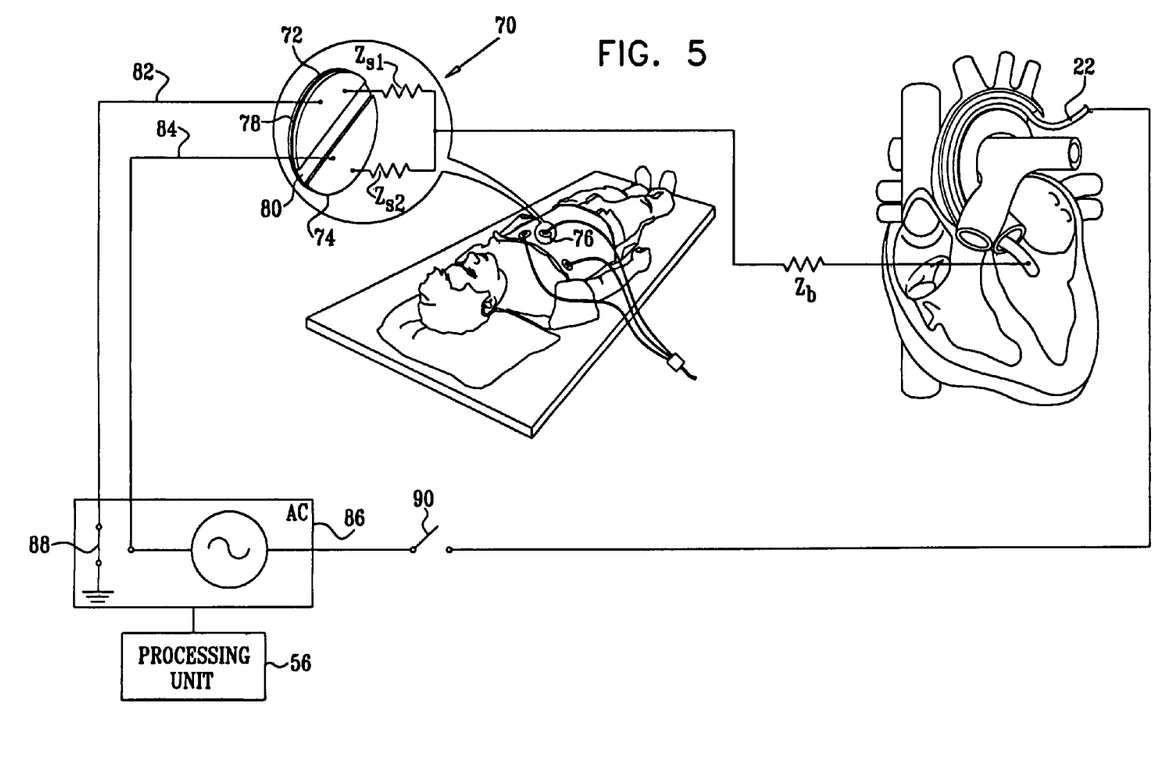
FIG. 5 is a schematic diagram showing the electroconductive body surface patch and circuitry of FIG. 4 configured in a calibration mode of operation in accordance with a disclosed embodiment of the invention.

Reference is now made to FIG. 5, which is a schematic diagram of the body surface patch 70 and its associated circuitry configured for a calibration mode of operation. FIG. 5 is similar to FIG. 4. However, the catheter 22 is now disconnected from the driver 86 by a switch 90. The switch 88 now connects the electrodes 72, 74 in a series circuit with the driver 86. Consequently, the driver 86 sees a calibration impedance $Z_{cal}$ in which the impedances $Z_{s1}$ and $Z_{s2}$ are in series. The processing unit 56 computes $Z_{cal}$ as follows:

$$Z_{cal} = Z_{s1} + Z_{s2}.$$

Assuming that $Z_{s1} \approx Z_{s2}$, then $Z_{cal} \approx 2Z_{s1}$, and $Z_{s1} \approx Z_{cal}/2$. When the switches 90, 88 are returned to the sensing configuration shown in FIG. 4, the processing unit 56, using the above relations, can compute the body impedance $Z_B$, compensating for the surface impedances as follows $$Z = Z_b + \frac{Z_{s1}}{2}, \text{ and}$$

$$Z_b = Z - \frac{Z_{cal}}{4}.$$

The processing unit 56 includes suitable interval timing circuitry or software for alternating the switches 90, 88 between the configurations of FIG. 4 and FIG. 5.

Optionally, if a change in the calibration impedance $Z_{cal}$ as determined in successive intervals exceeds a threshold, an alarm may be activated. Such an excursion may indicate electrode peel-off or disconnection, and in any case could impair the reliability of the respective body impedance measurement, even after compensation.

Operation

Figure 6:
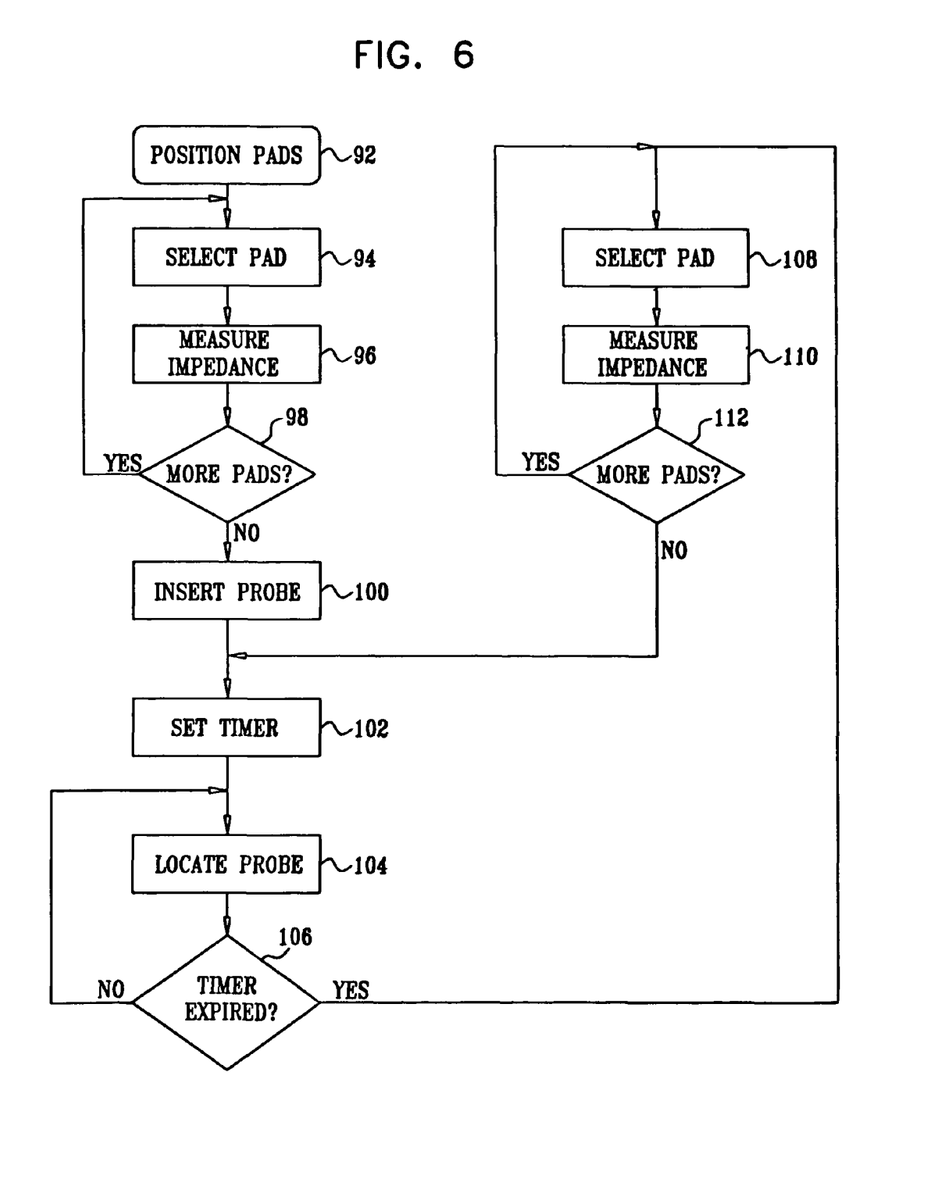
FIG. 6 is a flow chart illustrating a method of detecting body surface impedance of a living subject in accordance with a disclosed embodiment of the invention.

Reference is now made to FIG. 6, which is a flow chart illustrating a method of detecting body surface impedance while using impedance measurements to locate a probe inside a living subject in accordance with a disclosed embodiment of the invention. The process steps are shown in a particular sequence in FIG. 6 for clarity of presentation. However, it will be evident that many of them can be performed in parallel, asynchronously, or in different orders.

At initial step 92, dual-electrode body surface pads, as described above with reference to FIG. 4 and FIG. 5, are emplaced at convenient locations on the body surface of a subject, generally near the location of a probe to be inserted and mapped.

Next, at step 94 one of the body surface pads is chosen.

Next, at step 96 the electrodes of the current body surface pad are connected in a series circuit as shown in FIG. 5. A test current is passed from one of the electrodes to the other through the subject's skin or other body surface. The baseline impedance is measured and memorized.

Control now proceeds to decision step 98, where it is determined if more pads remain to be evaluated. If the determination at decision step 98 is affirmative, then control returns to step 94.

If the determination at decision step 98 is negative, then control proceeds to step 100. A probe is configured and inserted into an operational area of the body, for instance the left ventricle of the subject's heart.

Next, at step 102 an interval timer is set. The purpose of the timer is to establish a time interval, which, upon its passage, triggers a repeat of the impedance measurements that were performed in step 94, step 96, and decision step 98. The length of the interval is not critical. However, if the interval is too long, intervening changes in one or more of the body surface impedances may introduce errors in locating the probe. If the interval is too short, system overhead incurred in testing the body surface pads may limit the frequency at which measurements of the probe's position can be taken. Intervals of about one second have been found to be practical.

Next, at step 104 the position of the probe in the body is mapped by configuring the body surface pads as shown in FIG. 4, measuring impedances between the probe and the body surface pads, and performing triangulation as described above. In determining the impedances to be used for the triangulation calculations, the memorized values of the local impedances of the respective body surface pads are subtracted from the total impedance in order to determine the true intrabody impedances between the probe and the body surface. Thus, the effects of local variations in body surface impedance are eliminated. This increases the accuracy of the determination of the probe's position.

Control now proceeds to decision step 106, where it is determined if the timer that was set in step 102 has expired. If the determination at decision step 106 is negative, then control returns to step 104 to update the determination of the probe's location.

If the determination at decision step 106 is affirmative, then new measurements of the body surface impedances are to be taken. Control proceeds to a sequence of steps consisting of step 108, step 110, and decision step 112. These are performed identically to step 94, step 96 and decision step 98, respectively, and their details are not repeated in the interest of brevity. When the determination at decision step 112 indicates completion of the sequence, control returns to step 102, where the interval timer is reset. Position coordinates of the probe may now be determined by compensating for the updated body surface impedances, as described above.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus for position sensing, comprising:
   a probe, comprising at least one probe electrode, which is adapted to be inserted into a body of a living subject, said body having a body surface;
   a plurality of electroconductive body surface patches, which are adapted to be fixed to said body surface at respective surface locations, wherein said body surface patches each comprise a first electrode and a second electrode, said second electrode being electrically isolated from said first electrode;
   electrical circuitry having at least one switch for arranging said first electrode in a series circuit with said second electrode in a calibration mode of operation and for arranging said first electrode in a parallel circuit with said second electrode in a sensing mode of operation; and
   a controller, operative to control said electrical circuitry, wherein said controller is adapted to be coupled to said probe and to said body surface patches so as to pass first electrical signals through said first electrode and said second electrode thereof in said calibration mode of operation, and to pass respective second electrical signals through the body between said probe electrode and said body surface patches, wherein said controller is operative in said calibration mode of operation to determine a local electrical impedance of said body surface and of an interface thereof with a respective one of said body surface patches, and to determine position coordinates of said probe in said sensing mode of operation by measuring respective impedance characteristics of said second electrical signals, and wherein said impedance characteristics of said second electrical signals are adjusted by said controller according to respective instances of said local electrical impedance of said body surface.

2. The apparatus according to claim 1, wherein said controller is adapted to maintain a constant voltage between each of the surface locations and said probe electrode, and to measure said respective impedance characteristics by measuring currents at said constant voltage.

3. The apparatus according to claim 1, wherein said controller is adapted to maintain a constant current between each of the surface locations and said probe electrode, and to measure respective said impedance characteristics by measuring voltages at said constant current.

4. The apparatus according to claim 1, wherein said probe is adapted to perform a medical treatment on said subject.

5. The apparatus according to claim 1, wherein said body surface patches comprise an adhesive layer that contacts said body surface.

6. The apparatus according to claim 1, further comprising a timer, wherein said controller is operative to alternate said calibration mode of operation and said sensing mode of operation responsively to time intervals measured by said timer.

* * * * *